US011668776B2

(12) United States Patent
Kartäusch et al.

(10) Patent No.: US 11,668,776 B2
(45) Date of Patent: Jun. 6, 2023

(54) METHOD FOR PROVIDING A PROCESS PLAN OF A MAGNETIC RESONANCE EXAMINATION

(71) Applicant: Siemens Healthcare GmbH, Erlangen (DE)

(72) Inventors: Ralf Kartäusch, Bubenreuth (DE); Uvo Hölscher, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 127 days.

(21) Appl. No.: 17/212,309

(22) Filed: Mar. 25, 2021

(65) Prior Publication Data

US 2021/0302524 A1 Sep. 30, 2021

(30) Foreign Application Priority Data

Mar. 26, 2020 (DE) .................. 102020203958.5

(51) Int. Cl.
*G01R 33/54* (2006.01)
*G06F 16/22* (2019.01)
*G16H 70/20* (2018.01)

(52) U.S. Cl.
CPC .......... *G01R 33/546* (2013.01); *G06F 16/22* (2019.01); *G16H 70/20* (2018.01)

(58) Field of Classification Search
CPC ..... G01R 33/546; G01R 33/543; G06F 16/22; G16H 70/20; G16H 50/20; G16H 40/67; G16H 30/20; A61B 5/055; A61B 5/0033
See application file for complete search history.

(56) References Cited

U.S. PATENT DOCUMENTS

| 2007/0161871 A1 | 7/2007 | Haider et al. |
| 2017/0269181 A1* | 9/2017 | Aley .................. G01R 33/5607 |
| 2018/0068070 A1* | 3/2018 | Keil ........................ G16H 15/00 |

FOREIGN PATENT DOCUMENTS

DE        102005055657 A1      5/2007

OTHER PUBLICATIONS

German action dated Jan. 19, 2021, Application No. 10 2020 203 958.5.

* cited by examiner

*Primary Examiner* — Susan S Lee
(74) *Attorney, Agent, or Firm* — Banner & Witcoff Ltd.

(57) ABSTRACT

Techniques are disclosed for providing a process plan of a magnetic resonance examination incorporating n protocols where n≥1. The process plan includes selecting an examination strategy with a number n of metaprotocols and a chronological order of the n metaprotocols. Each of the n metaprotocols includes a protocol category having a plurality of different variants of a protocol of the one protocol category. The process plan further includes selecting a variant of a protocol of the one protocol category of an ith metaprotocol, where 1≤i≤n, repeating the step of selecting the variant of a protocol of the one protocol category of an ith metaprotocol until i=n, and providing the magnetic resonance examination process plan including the n protocols.

17 Claims, 2 Drawing Sheets

Figure 1:
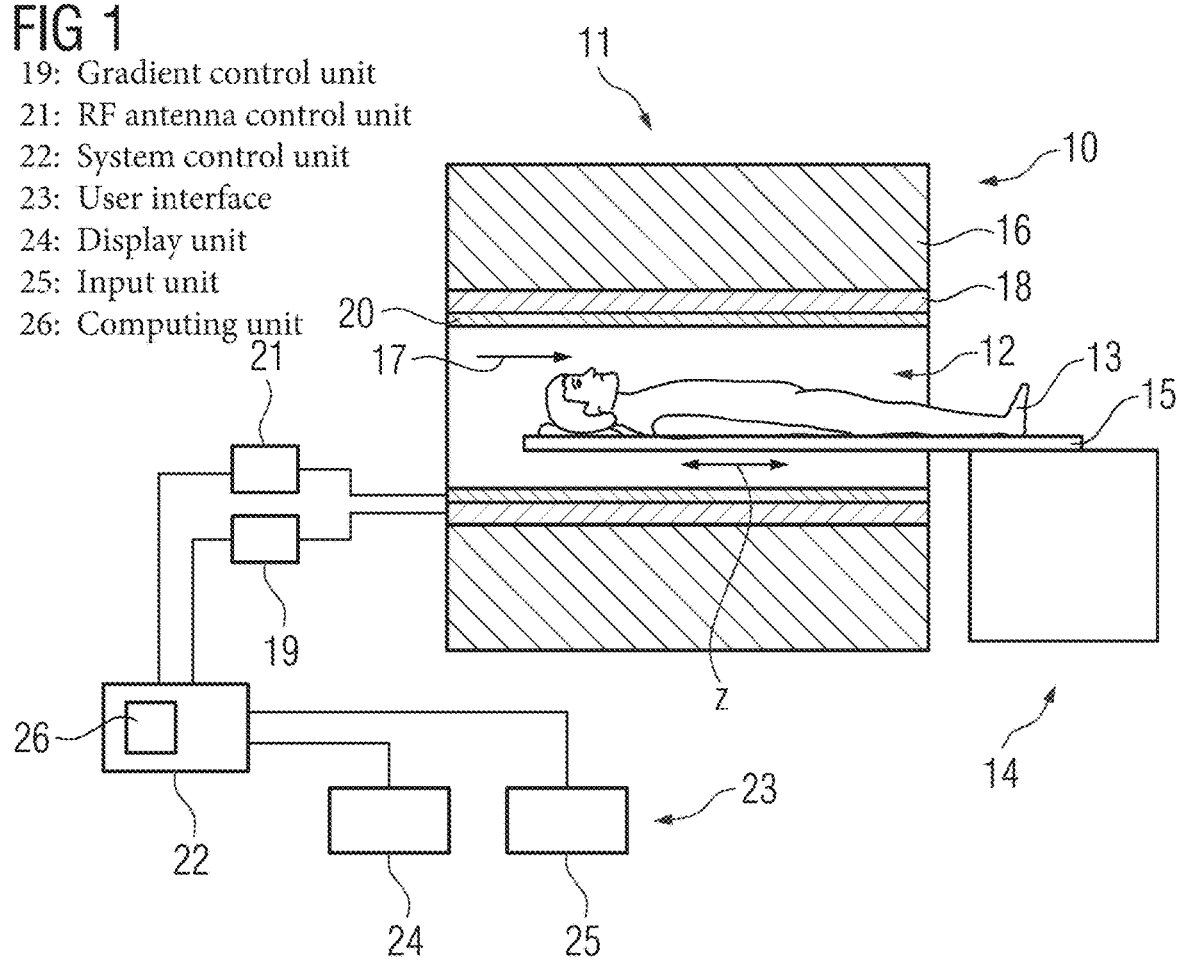

19: Gradient control unit
21: RF antenna control unit
22: System control unit
23: User interface
24: Display unit
25: Input unit
26: Computing unit 19: Gradient control unit
21: RF antenna control unit
22: System control unit
23: User interface
24: Display unit
25: Input unit
26: Computing unit 100 Select examination strategy
101 Select a variant of a protocol P
102 Provide a process plan of the MR examination
103 Perform MR examination

METHOD FOR PROVIDING A PROCESS PLAN OF A MAGNETIC RESONANCE EXAMINATION

CROSS-REFERENCE TO RELATED APPLICATIONS

The present application claims the benefit of the filing date of German patent application no. DE 10 2020 203 958.5, filed on Mar. 26, 2020, the contents of which are incorporated herein by reference in their entirety.

TECHNICAL FIELD

The disclosure relates to a method for providing a process plan of a magnetic resonance examination. The present disclosure also relates to a magnetic resonance apparatus comprising a scanner unit and a computing unit, wherein the computing unit is designed and/or set up to carry out the method for providing a process plan of a magnetic resonance examination. The disclosure also relates to a computer program product comprising a program directly loadable into a memory of a computing unit and having a program means for carrying out a method for providing a process plan of a magnetic resonance examination when the program is executed in the control unit.

BACKGROUND

In order to be able to perform a magnetic resonance examination on a patient, a user, in particular a medical operator, must first make a selection regarding an examination strategy and a process plan. This examination strategy and/or process plan may comprise a plurality of protocols and their order relative to one another. It has conventionally been common practice to provide all the possible process plans containing possible combinations of protocols and/or different variants of protocols as stored process plans, so that a predefined process plan is available for each examination strategy.

The different variants of a protocol may differ with respect to a hardware attribute, e.g. a hardware attribute of hardware available for the magnetic resonance examination. In addition, the different variants of a protocol may also differ with respect to license availability. For example, a license specifies whether a protocol may be executed with or without certain attributes, and thus may be considered as defining the permissions or concessions of which attributes are to be executed for a particular protocol. For example, a license may relate to a sequence feature or the entire protocol or even the entire process plan. Moreover, the different variants of a protocol may also differ in respect of sequence attributes. For example, whether 2D image data or 3D image data is to be acquired.

The plethora of different hardware attributes and the large number of possible licenses results in an enormous number of available combinations, all of which are stored in a memory unit and/or a database. The individual variants of a process plan are stored in a directory tree where they can be selected by a user. However, this complexity makes it difficult for the user to select the best possible process plan for a magnetic resonance examination.

SUMMARY

The object of the present disclosure is to provide simple and quick selection of a best possible process plan for a magnetic resonance examination. This object is achieved by the embodiments as described herein and the claims. The disclosure proceeds from a method for providing a process plan of a magnetic resonance examination, wherein the process plan includes n protocols where $n \geq 1$, comprising the following steps:

Selecting an examination strategy comprising a number n of metaprotocols and a chronological order of the n metaprotocols, wherein each of the n metaprotocols comprises one protocol category containing a plurality of different variants of a protocol of the one protocol category;

selecting a variant of a protocol of the one protocol category of an ith metaprotocol, where $1 \leq i \leq n$;

repeating the step of selecting the variant of a protocol of the one protocol category of an ith metaprotocol until $i=n$; and providing the magnetic resonance examination process plan comprising the n protocols.

A magnetic resonance examination of a patient, in particular of a region of interest of the patient, is designed to clarify a clinical and/or medical issue. Here, a process plan of a magnetic resonance examination describes in particular a workflow, wherein the process plan and/or workflow defines an order of the individual protocols and/or metaprotocols during performance of the magnetic resonance examination. In particular, by means of the process plan and/or workflow, a procedure for the upcoming and/or planned magnetic resonance examination can be determined or rather, by selecting an examination strategy, the process plan and/or workflow is determined for the upcoming and/or planned magnetic resonance examination and/or for the clinical and/or medical issue. For example, by defining the examination strategy, a contrast to be used can be defined in the protocols, such as a T1 contrast and/or a T2 contrast and/or a diffusion, etc. In addition, by defining the examination strategy, an orientation to be used can also be specified, such as a sagittal orientation and/or a coronal orientation and/or a transverse orientation and/or a tilted orientation, etc.

In addition, by selecting the examination strategy, it can also be specified whether the upcoming and/or planned magnetic resonance examination is to comprise a 2D measurement or a 3D measurement or if a measurement is also to be performed that is insensitive to movements of the patient, etc. When selecting the examination strategy, it may also be possible for the user to enter such information together with the selection of the examination strategy. Moreover, other characteristics of the magnetic resonance examination can also be specified within the process plan and/or the workflow, such as whether to perform a fast measurement and/or a measurement with a high resolution and/or a measurement that is robust and/or insensitive to patient movement, etc. For a magnetic resonance examination, the process plan and/or workflow is executed using the selected protocols in order to obtain medical imaging data to answer clinical and/or medical questions.

A protocol comprises a set of values required to describe a specific form of a sequence. Typical values in this regard may include an echo time (TE), a repetition time (TR), a field of view, a matrix size, a number of slices, a fat saturation method, an acceleration method, a local RF antenna unit, etc. Such values of a protocol are often also highly dependent on the locally-available hardware and/or design of the magnetic resonance apparatus, such as a gradient strength of the magnetic resonance apparatus and/or number of acquisition channels, etc. A protocol thus describes a very specific way of acquiring an image using a very specific design of a magnetic resonance apparatus. In particular, a contrast and/or a geometry and a measuring time are matched to the clinical issue to be investigated by the upcoming magnetic resonance examination.

A sequence for a magnetic resonance examination comprises in particular a logical succession of radio frequency (RF) pulses, gradient pulses and acquisition periods for controlling data acquisition for magnetic resonance data capture. This sequence defines the basic magnetic resonance mechanisms used in magnetic resonance data acquisition, such as a gradient echo or spin echo, a steady state of magnetization, preparation pulses, etc. Typical and well-known sequences include a spin-echo sequence (SE sequence), a turbo spin-echo sequence (TSE sequence), an echo planar imaging (EPI) sequence, etc. However, a sequence does not define the complete time pattern of all the RF pulses, gradient pulses and acquisition periods, but only their interaction. In principle, a parameterization of a sequence can be adjusted e.g. by a user and/or a medical operator. In particular, the sequence timing and/or sequence resolution can be adapted to suit the clinical and/or medical issue under investigation.

A metaprotocol comprises a protocol category intended to clarify a clinical issue. A metaprotocol e.g. comprises a single protocol category. For example, a protocol category can include a transverse T1 measurement for a knee or other protocol categories. The metaprotocol additionally comprises a plurality of different variants of a protocol of the one protocol category. The protocol categories of the different metaprotocols may be different from each other. For example, the different variants of the protocol of the one protocol category may differ with respect to hardware attributes of the hardware available for the magnetic resonance examination. In addition, the different variants of the protocol of the one protocol category may differ with respect to license-related attributes, e.g. as to whether a step covered by a license may or may not be executed. In addition, the metaprotocol may comprise variants of a protocol of the one protocol category that can be derived by means of a rule from an already existing variant of a protocol of the one protocol category of the metaprotocol. Selection of a variant of a protocol of the one protocol category of a first metaprotocol may be independent of the selection of a variant of a protocol of the one protocol category of a second metaprotocol.

The individual variants of a protocol of the one protocol category may be stored in a memory unit and/or a database. The memory unit and/or the database can be incorporated in the magnetic resonance imaging apparatus performing the magnetic resonance examination. In addition, it is also conceivable for the database and/or the memory unit to be external to the magnetic resonance apparatus. It is also possible for said database and/or memory unit to be stored in a cloud. The magnetic resonance apparatus e.g. a computing unit of the magnetic resonance apparatus, may access the database and/or the memory unit via a data link in this case.

The examination strategy e.g. comprises a number n of metaprotocols that are required to clarify the clinical and/or medical issue for the upcoming magnetic resonance examination. In addition to the number n of metaprotocols, the examination strategy also comprises a chronological order of the individual metaprotocols of the n metaprotocols with respect to each other. This also determines the sequence in which the individual protocols are executed. The examination strategy may be selected by a user, e.g. a medical operator. The selection of the examination strategy may be made by the user, e.g. the medical operator, on an input unit of the magnetic resonance apparatus. By determining the examination strategy, the number of metaprotocols and also their sequence is determined, e.g. automatically and/or autonomously by means of a computing unit of the magnetic resonance apparatus.

The selection of a variant of a protocol of the one protocol category of the ith metaprotocol may be performed automatically or autonomously by means of the computing unit. The variant of a protocol of the one protocol category is selected from the plurality of different variants of the protocol of the one protocol category for each metaprotocol of the n metaprotocols by means of the computing unit. The computing unit here may use supplied and/or stored information. This information may be information concerning hardware attributes of the hardware available locally for the magnetic resonance examination. In addition, the information may include license information. Furthermore, the information may include information entered by a user, e.g. as to whether a user wishes to use a 2D measurement or a 3D measurement to clarify the clinical and/or medical issue. The step of selecting a variant of a protocol of the one protocol category is repeated for each metaprotocol encompassed by the selected examination strategy until a variant of a protocol is selected for all n metaprotocols, and n selected protocols are available for performing the magnetic resonance examination. The process starts with i=1, i.e. with a first metaprotocol. With each repetition, i is increased by 1 until i=n and thus a selected variant of a protocol has been determined and/or is available for all n metaprotocols.

The process plan of the magnetic resonance examination is also provided by means of the computing unit of the magnetic resonance apparatus, e.g. it is provided automatically and/or autonomously by means of the computing unit. Here, it can also be provided that the provided process plan of the magnetic resonance examination with the n protocols is presented to the user by means of a user interface, e.g. an indicator unit with a display and/or monitor. The provided process plan of the magnetic resonance examination with the n protocols is therefore ready for performing the magnetic resonance examination.

The method according to the disclosure for providing a process plan of a magnetic resonance examination may be controlled and/or carried out by means of the computing unit. Here, individual steps of the method according to the disclosure can be carried out directly by the computing unit. In addition, individual steps of the method according to the disclosure can also be carried out by other units, but controlled by the computing unit.

The computing unit comprises at least one computing module and/or processor, wherein the computing unit for carrying out the method is designed to provide a process plan of a magnetic resonance examination. For instance, the computing unit is designed to execute computer-readable instructions for carrying out the method according to the disclosure for providing a process plan of a magnetic resonance examination. As an example, the computing unit comprises a memory unit, wherein computer-readable information is stored on the memory unit, wherein the computing unit is designed to load the computer-readable information from the memory unit and to execute the computer-readable information in order to perform a method according to the disclosure for providing a process plan of a magnetic resonance examination. In this way, the computing unit according to the disclosure is designed to carry out a method for providing a process plan of a magnetic resonance examination.

The components of the computing unit can be largely implemented in the form of software components. In principle, however, especially if particularly fast calculations are involved, some of these components can also be implemented in the form of software-based hardware components such as FPGAs or similar. Likewise, the required interfaces can be designed as software interfaces, e.g. if only transferring data from other software components is involved. However, they can also be designed as hardware interfaces that are controlled by suitable software. Self-evidently, it is also conceivable for a plurality of the aforementioned components to be combined in the form of a single software component or software-based hardware component.

The embodiments of the disclosure have the advantage that an optimum process plan for a magnetic resonance examination can be selected particularly easily and quickly. For instance, the disclosure enables an optimum process plan for a magnetic resonance examination to be selected automatically and/or autonomously by means of the computing unit. For instance, it also enables complexity in the selection and/or provision of a magnetic resonance examination to be reduced, since a protocol selection is made for each metaprotocol individually, which selection is independent of the other metaprotocols, e.g. of a protocol selection of the other metaprotocols. In this way, protocol selection can also be simplified for inexperienced operators. In addition, storage space available for the provision can also be reduced, since the disclosure means that all the possible combinations of protocol variants for a magnetic resonance examination are no longer already stored in preconfigured form.

In an advantageous development of the method according to the disclosure it can be provided that selection logic is available which performs selection of a variant of the protocol of the one protocol category of the ith metaprotocol. The selection logic may be incorporated in the computing unit. The selection logic can comprise software and/or computer programs executed by the computing unit for selecting a variant of a protocol of the one protocol category of the ith metaprotocol. Selection of a variant of the protocol of the one protocol category of the ith metaprotocol may be executed and/or performed by the selection logic on the basis of information, e.g. selection information. The selection information can include information regarding a hardware attribute of available hardware and/or information regarding a license attribute and/or other selection information.

The selection logic can also comprise a machine learning method, also called deep learning, which is based on an artificial neural network. In particular, an artificial neural network (ANN) is a network of artificial neurons simulated in a computer program. The artificial neural network is typically based on a network of a plurality of artificial neurons. The artificial neurons are typically disposed on different layers. The artificial neural network usually comprises an input layer and an output layer, the neuron output of which is the only one visible in the artificial neural network. Layers between the input layer and the output layer are typically referred to as hidden layers. Typically, an artificial neural network architecture and/or topology is first initialized and then trained for a specific task or for multiple tasks in a training phase. This training of the artificial neural network typically includes changing a weighting of a connection between two artificial neurons of the artificial neural network. Training of the artificial neural network may also include developing new connections between artificial neurons, deleting existing connections between artificial neurons, adjusting threshold values of the artificial neurons, and/or adding or deleting artificial neurons. As an example, the artificial neural network may already be suitably trained in advance to select a variant of the protocol of the one protocol category of the ith metaprotocol.

In this way, a variant of a protocol of the one protocol category of the ith metaprotocol can be selected particularly quickly and provided to a user, e.g. to a medical operator. This can also advantageously prevent time-consuming, manual searching for a corresponding combination of protocols from a protocol tree.

In an advantageous development of the method according to the disclosure, it can be provided that the selection logic selects a variant of the protocol of the one protocol category of the ith metaprotocol according to a hardware attribute of hardware available for performing the magnetic resonance examination. The hardware attribute can comprise, for example, an available configuration of the magnetic resonance apparatus. For instance, the hardware attribute can comprise a strength of a main magnetic field and/or a maximum strength of a gradient field and/or a number of coil channels and/or available local RF antenna units, e.g. local coils, etc. In this way, selection of an optimum process plan for a magnetic resonance examination can be provided particularly simply and quickly according to the hardware available locally or more specifically the magnetic resonance apparatus available locally.

In an advantageous development of the method according to the disclosure, it can be provided that, prior to selection of a variant of the protocol of the one protocol category of an ith metaprotocol, the hardware attribute is determined by means of the selection logic. The hardware attribute may be stored and/or deposited in a database and/or a memory unit and is interrogated and/or retrieved, e.g. automatically interrogated and/or retrieved, by the selection logic prior to selection of a variant of a protocol of the one protocol category of the ith metaprotocol. In addition, it can also be the case that the hardware attribute is determined by means of a query. Such a query can take place, for example, at regular intervals, such as e.g. quarterly or bi-annually, etc. This embodiment makes it possible for the hardware attribute of available hardware to be quickly available for automatic and/or autonomous selection of a variant of a protocol of the one protocol category of an ith metaprotocol.

In an advantageous development of the method according to the disclosure, it can be provided that the selection logic selects a variant of the protocol of the one protocol category of the ith metaprotocol depending on license information. The license information may comprise information as to whether at least one defined step may be performed when the variant of the protocol of the one protocol category of the ith metaprotocol is executed. For instance, the license information comprises information about a right of use for performing at least one defined step of the variants of the protocol of the one protocol category of the ith metaprotocol. This advantageously provides a particularly easy and quick mean of selecting an optimum process plan for a magnetic resonance examination using the locally available license attributes.

In an advantageous development of the method according to the disclosure it can be provided that, prior to selection of a variant of the protocol of the one protocol category of the ith metaprotocol, the license information is determined by means of the selection logic. The license information may be stored and/or deposited in a database and/or a memory unit and is interrogated and/or retrieved by the selection logic before a variant of a protocol of the one protocol category of the ith metaprotocol is selected. In addition, it is also possible for the license information to be determined by means of a query. For example, such a query can be made at regular intervals, e.g. monthly, etc. This embodiment enables the license information to be quickly available for automatic and/or autonomous selection of a variant of a protocol of the one protocol category of an ith metaprotocol.

In an advantageous development of the method according to the disclosure, it can be provided that the ith metaprotocol comprises two or more different variants of a protocol of the one protocol category, wherein the two or more different variants of the protocol of the one protocol category are stored in a database. This database can be located within the computing unit which e.g. comprises the selection logic and/or can be comprised by the computing unit. In addition, it is also conceivable for the database to be implemented separately from the computing unit, but encompassed by the magnetic resonance apparatus. The database can also be implemented externally to the magnetic resonance apparatus. For example, the database can be located in a cloud. In this case, the computing unit, e.g. the selection logic, can access the database by means of a data interface and/or a data link.

This embodiment of the disclosure allows fast access to the two or more different variants of a protocol of the one protocol category of the ith metaprotocol for automatic and/or autonomous selection of a variant of a protocol of the one protocol category of the ith metaprotocol by the computing unit, e.g. the selection logic.

In an advantageous development of the method according to the disclosure, it can be provided that the two or more different variants of the protocol of the one protocol category of the ith metaprotocol are different in respect of a sequence parameter and/or a sequence attribute, wherein the selection logic selects a variant of the protocol of the ith metaprotocol of the one protocol category depending on the sequence parameter and/or the sequence attribute. For example, the sequence parameter and/or sequence attribute can include whether the variant of the protocol comprises a 2D sequence or a 3D sequence. In addition, further refinement of the sequence parameters and/or the sequence attribute is possible at any time. For example, the sequence attribute and/or the sequence parameter may already be determined when the examination strategy is selected. In this way, a corresponding variant of a protocol of the one protocol category of the ith metaprotocol can be automatically selected and provided by the selection logic particularly quickly, thereby obviating time-consuming manual selection of a corresponding combination of protocols from a protocol tree.

In an advantageous development of the method according to the disclosure, it can be provided that at least one of the n metaprotocols comprises a minimum variant of a protocol of the one protocol category, wherein the minimum variant of the protocol of the one protocol category is available for selecting a variant of the protocol of the one protocol category. Each metaprotocol of the n metaprotocols may comprise a minimum variant of a protocol of the one protocol category. The minimum variant of a protocol of the one protocol category may comprise a protocol variant that comprises minimum requirements for existing and/or available hardware and/or minimum requirements for available licenses, such as no existing licenses. As an example, the minimum variant of a protocol of the one protocol category comprises a protocol variant that is executable on each scanner unit of a magnetic resonance apparatus independently of existing and/or available license attributes and/or independently of hardware attributes, e.g. independently of the locally existing and/or available hardware. This means that an executable variant of a protocol of the one protocol category of the ith metaprotocol can always be available, said variant of the protocol being executable independently of a license attribute and/or hardware attributes.

In an advantageous development of the method according to the disclosure it can be provided that at least one of the n metaprotocols comprises a maximum variant of a protocol of the one protocol category, wherein the maximum variant of the protocol of the one protocol category is available for selecting a variant of the protocol. Each metaprotocol of the n metaprotocols e.g. comprises a maximum variant of a protocol of the respective protocol category. The maximum variant of a protocol of the one protocol category may comprise a "best variant" and/or an "ideal variant" of a protocol of the one protocol category. As an example, the maximum variant of a protocol of the one protocol category comprises a protocol variant that assumes maximum available hardware components and/or maximum possible license attributes. Thus, the maximum variant of a protocol of the one protocol category comprises the protocol variant that provides the most ideal image data for clarifying the clinical and/or medical issue when the protocol variant is executed. If all the licensing requirements are met and maximum available hardware components are available, the maximum variant of a protocol of the one protocol category may be selected automatically by the selection logic when selecting a variant of a protocol for the ith metaprotocol.

In an advantageous development of the method according to the disclosure it can be provided that the ith metaprotocol comprises a first variant of a protocol of the one protocol category, wherein the first variant of the protocol of the one protocol category is stored in a database, and the selection logic generates and/or creates a second variant of the protocol of the one protocol category from the first variant of the protocol of the one protocol category by means of a defined rule. The second variant of a protocol of the one protocol category for the ith metaprotocol may be generated and/or created automatically and/or autonomously by means of the selection logic. The second variant of a protocol of the one protocol category is generated and/or created from the first variant of a protocol of the one protocol category if no variant of a protocol of the one protocol category is stored for a corresponding hardware attribute and/or software attribute.

This enables only a limited number of variants of a protocol of the one protocol category for a metaprotocol to be stored and/or deposited in the database, thereby also saving storage space. In addition, dynamic adaptation of the ith metaprotocol to changing hardware attributes and/or license attributes can be advantageously achieved.

The defined rule may comprise a set (e.g. predetermined) rule that generates another variant of a protocol of the one protocol category based on an existing variant of a protocol of the one protocol category. For example, the first variant of the protocol of the one protocol category can have a licensed step Y and/or a licensed feature Y. The defined rule specifies generating a new variant of the protocol of the one protocol category from the existing variant of the protocol of the one protocol category by omitting the licensed step Y and/or the licensed feature Y. In addition, the defined rule can include further changes to the existing variant of the protocol of the one protocol category, such as, for example, when licensed step Y and/or licensed feature Y is omitted and a parameter and/or a value Z is changed. For example, the first variant of a protocol of the one protocol category may comprise a TSE T1 protocol having an SMS (Simultaneous Multi Slice) license. In this case, the defined rule for generating and/or creating a second protocol of the one protocol category can include omitting the SMS license and additionally reducing a number of layers by 30% for example.

In an advantageous development of the method according to the disclosure it can be provided that, by means of the selection logic, at least one new variant of a protocol of the one protocol category of the ith metaprotocol is created and/or generated and this new variant of the protocol of the one protocol category is stored in a database. In this way, dynamic adaptation of the ith metaprotocol to changes in the hardware and/or to license changes and/or to software changes can be advantageously achieved.

In an advantageous development of the method according to the disclosure it can be provided that the selection of a variant of a protocol of the one protocol category of the ith metaprotocol is independent of selection of a variant of a protocol of the one protocol category of an (i+1)th metaprotocol. This enables a process plan for a magnetic resonance examination to be structured in a particularly flexible manner. For example, in the case of a license change that affects only one or a small number of metaprotocols, only these metaprotocols can be adapted. This has the additional advantage that not all the possible combinations of protocols, said combinations including a protocol affected by the license change, need to be adapted and stored again.

The disclosure also relates to a magnetic resonance examination using a scanner unit and a computing unit, wherein the computing unit comprises selection logic and is designed to carry out a method for providing a process plan of a magnetic resonance examination comprising n protocols.

The magnetic resonance apparatus may comprise a medical and/or diagnostic magnetic resonance apparatus designed and/or set up to acquire medical and/or diagnostic image data. The scanner unit of the magnetic resonance apparatus may comprise a detector unit, e.g. a magnet unit, for acquiring medical and/or diagnostic image data. Said scanner unit, e.g. the magnet unit, may comprise a main magnet, a gradient coil unit, and an RF antenna unit.

The scanner unit of the magnetic resonance apparatus at least partially encloses a patient receiving region of the magnetic resonance apparatus. For example, the patient receiving region can be cylindrical and/or surrounded cylindrically by the scanner unit. A field of view (FOV) and/or an isocenter of the magnetic resonance apparatus may be located within the patient receiving region. The FOV may comprise an acquisition area of the magnetic resonance apparatus within which ideal conditions exist for acquiring medical image data within the patient receiving region.

The isocenter of the magnetic resonance apparatus may comprise the region and/or point within the magnetic resonance apparatus that has the most optimal and/or ideal conditions for acquiring medical image data. For example, the isocenter comprises the most homogeneous magnetic field region within the magnetic resonance apparatus. For a magnetic resonance examination, the patient, e.g. the region of the patient to be examined, is disposed and/or positioned within the patient receiving region. For this purpose, the patient is first positioned on the patient table. The patient table is then moved into the patient receiving region together with the patient positioned thereon until the region of the patient to be examined is located in the FOV and/or in the isocenter of the magnetic resonance apparatus, in particular of the scanner unit.

The advantage of such a magnetic resonance apparatus is that selection of an optimum process plan for a magnetic resonance examination can be provided particularly easily and quickly. As an example, the disclosure enables an optimum process plan for a magnetic resonance examination to be selected automatically and/or autonomously by means of the computing unit. For instance, complexity involved in the selection and/or provision of a magnetic resonance examination can be reduced in such a way that a protocol selection is made for each metaprotocol individually, which selection is independent of the other metaprotocols, e.g. of protocol selection of the other metaprotocols. In this way, protocol selection can also be simplified for inexperienced operators. In addition, storage space available for the provision thereof can also be reduced, since the disclosure means that all the possible combinations of protocol variants for a magnetic resonance examination are no longer already stored in a pre-configured manner.

The advantages of the magnetic resonance apparatus according to the disclosure essentially correspond to the advantages of the method according to the disclosure for providing a process plan of a magnetic resonance examination comprising n protocols, as set out previously in detail. Features, advantages or alternative embodiments mentioned herein can likewise be applied to the other claimed objects, and vice versa.

The disclosure also relates to a computer program product comprising a program directly loadable in a memory of a programmable computing unit (e.g. a non-transitory computer-readable medium) and having program means for carrying out a method for providing a process plan of a magnetic resonance examination comprising n protocols when the program is executed in the computing unit. Said computer program may require program means, e.g. libraries and auxiliary functions, in order to implement the corresponding embodiments of the method. The computer program may comprise software having a source code that still has to be compiled and bound or only has to be interpreted, or an executable software code that only has to be loaded into a corresponding computing unit for execution.

The computer program product according to the disclosure is directly loadable into a memory of a programmable computing unit and has program code means for carrying out a method according to the disclosure for providing a process plan of a magnetic resonance examination comprising n protocols when the computer program product is executed in the computing unit. The computer program product can be or can comprise a computer program. As a result, the method according to the disclosure can be executed in a fast, identically repeatable, and robust manner. The computer program product is configured such that it can perform the method steps according to the disclosure by means of the computing unit. The computing unit must in each case possess the prerequisite elements, such as a corresponding main memory, a corresponding graphics card or a corresponding logic unit, so that the respective method steps can be carried out efficiently. The computer program product is stored e.g. on a computer-readable medium or provided on a network or server from where it can be loaded into the processor of a local computing unit which can be directly connected to the magnetic resonance apparatus or implemented as a part thereof.

In addition, control information of the computer program product can be stored on an electronically readable data carrier. The control information of the electronically readable data carrier can be configured to carry out a method according to the disclosure when the data carrier is used in a computing unit. Thus, the computer program product may also constitute the electronically readable data carrier. Examples of electronically readable data carriers are a DVD, a magnetic tape, a hard disk or a USB stick on which electronically readable control information, in particular software (cf. above), is stored. If this control information (software) is read from the data carrier and stored in a control and/or computing unit, all the embodiments of the methods described above can be carried out. Thus, the disclosure can also relate to said computer-readable medium and/or said electronically readable data carrier.

In addition, the disclosure relates to a computer-readable data carrier comprising a program designed to carry out a method for providing a process plan of a magnetic resonance examination comprising n protocols.

BRIEF DESCRIPTION OF THE DRAWINGS/FIGURES

Figure 2:
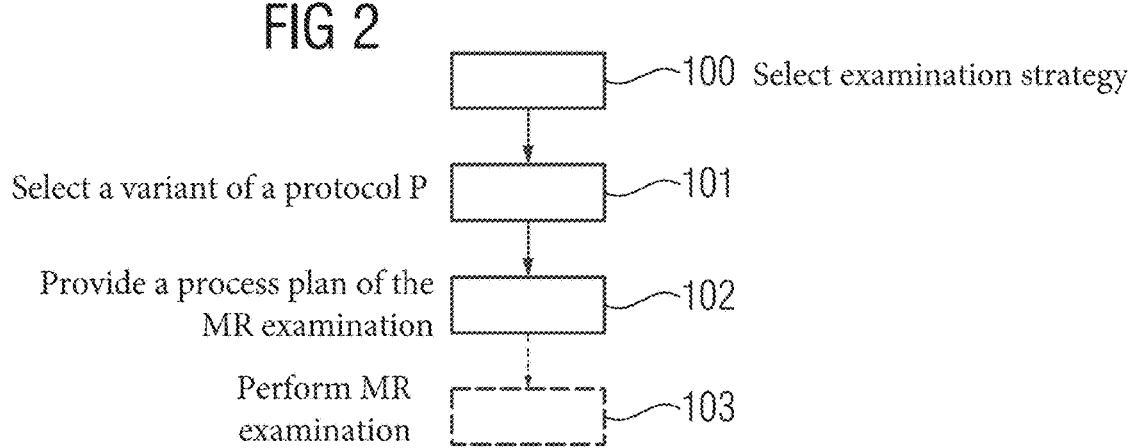
Figure 3:
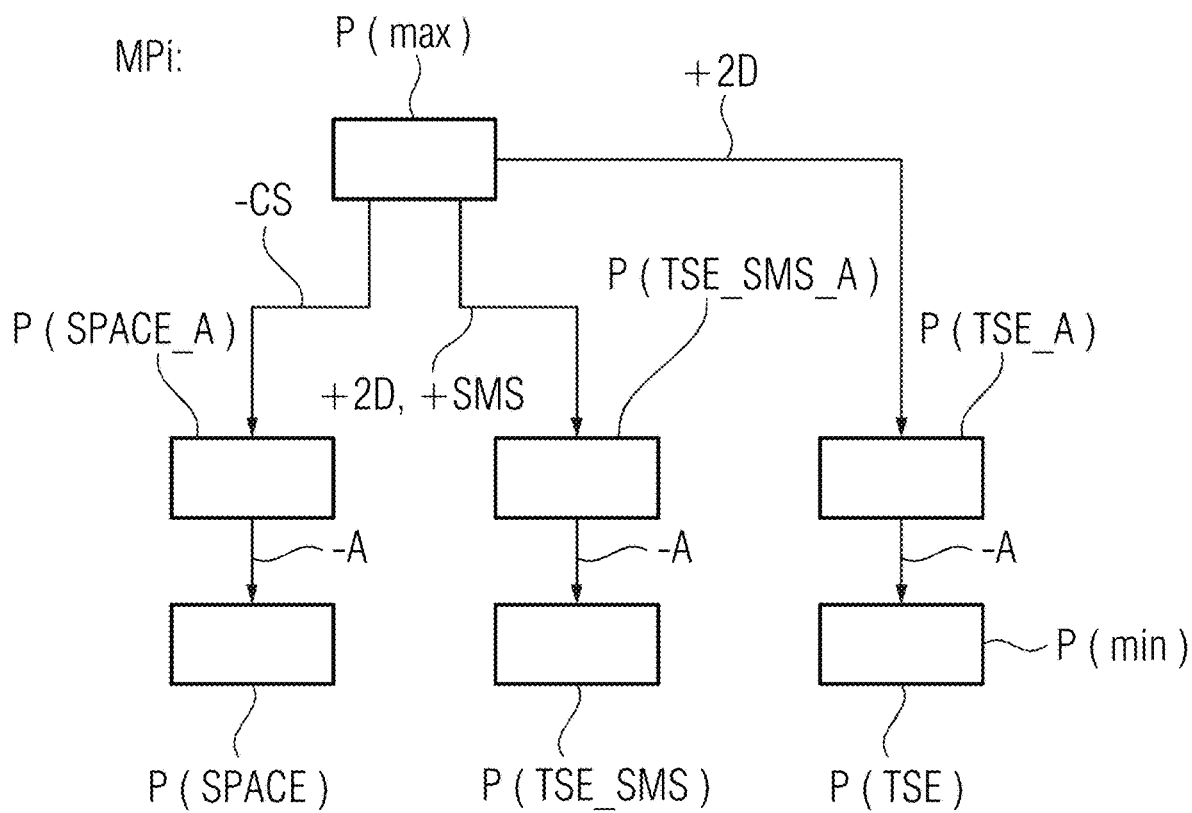
Figure 4:
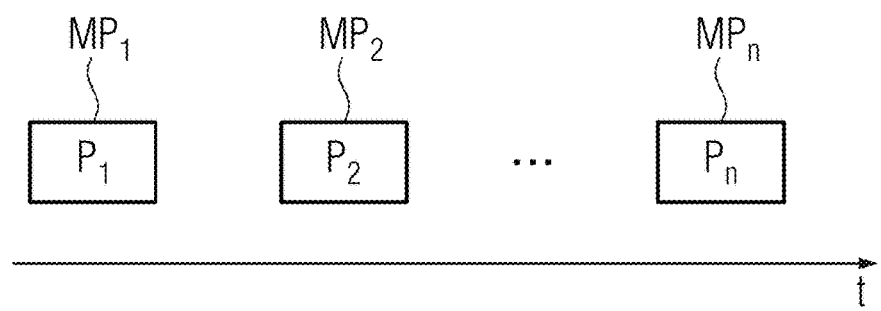

The accompanying drawings form a part of this disclosure, and are intended to be of assistance in gaining further understanding of the present disclosure. These drawings illustrate embodiments of the present disclosure, and together with the disclosure are intended to explain the principles of the embodiments of the present disclosure. In the drawings, identical components are indicated using identical labels. Further advantages, features and details of the disclosure will emerge from the exemplary embodiment described below and from the associated drawings in which:

FIG. 1 schematically illustrates a magnetic resonance apparatus according to the one or more embodiments of the present disclosure, FIG. 2 shows a method according to the one or more embodiments of the present disclosure for providing a process plan of a magnetic resonance examination, FIG. 3 shows a view of a metaprotocol comprising a plurality of different variants of a protocol, in accordance with one or more embodiments of the present disclosure; and FIG. 4 shows a process plan of a magnetic resonance examination comprising a plurality of protocols, in accordance with one or more embodiments of the present disclosure.

DETAILED DESCRIPTION

FIG. 1 schematically illustrates a magnetic resonance apparatus 10. The magnetic resonance apparatus 10 comprises a scanner unit 11 constituted by a magnet unit. The magnetic resonance apparatus 10 also comprises a patient receiving region 12 for accommodating a patient 13. The patient receiving region 12 in this exemplary embodiment is cylindrical in shape and is surrounded cylindrically in a circumferential direction by the scanner unit 11, e.g. by the magnet unit. In principle, however, a design of the patient receiving region 12 deviating from this is also conceivable. The patient 13 can be slid and/or moved into the patient receiving region 12 by means of a patient positioning device 14 of the magnetic resonance apparatus 10. For this purpose, the patient positioning device 14 comprises a patient table 15 which is designed to be movable within the patient receiving region 12. For instance, the patient table 15 may be mounted so as to be movable in the direction of a longitudinal extension of the patient receiving region 12 and/or in the z-direction.

The scanner unit 11, e.g. the magnet unit, comprises a superconducting main magnet 16 for generating a powerful and in particular constant main magnetic field 17. The scanner unit 11, e.g. the magnet unit, also has a gradient coil unit 18 for generating magnetic field gradients which are used for position encoding during imaging. The gradient coil unit 18 is controlled by means of a gradient control unit 19 of the magnetic resonance apparatus 10. The scanner unit 11, e.g. the magnet unit, also comprises an RF antenna unit 20 for exciting a polarization which arises in the basic magnetic field 17 generated by the basic magnet 16. The RF antenna unit 20 is controlled by an RF antenna control unit 21 of the magnetic resonance apparatus 10 and radiates RF magnetic resonance sequences into the patient receiving region 12 of the magnetic resonance apparatus 10.

The magnetic resonance apparatus 10 has a system control unit 22 for controlling the main magnet 16, the gradient control unit 19 and the RF antenna control unit 21. The system control unit 22 centrally controls the magnetic resonance apparatus, e.g. for performing a predetermined imaging gradient echo sequence. The system control unit 22 also comprises an evaluation unit (not shown in more detail) for evaluating medical image data acquired during the magnetic resonance examination.

In addition, the magnetic resonance apparatus 10 comprises a user interface 23 connected to the system control unit 22. Control information such as, for example, imaging parameters as well as reconstructed magnetic resonance images can be displayed to a medical operator on a display unit 24, e.g. on at least one monitor, of the user interface 23. The user interface 23 also comprises an input unit 25 by means of which information and/or parameters can be entered by the medical operator during a measurement process.

The magnetic resonance apparatus 10 may comprise other components normally found in magnetic resonance equipment 10. Moreover, as a general mode of operation of a magnetic resonance apparatus 10 will be well known to persons skilled in the art, the other components will not be described in detail.

FIG. 2 shows a method according to the one or more embodiments of the disclosure for providing a process plan of a magnetic resonance examination. The process plan of the magnetic resonance examination comprises n protocols, where n≥1. The method for providing a process plan of a magnetic resonance examination is controlled by a computing unit 26 of the magnetic resonance apparatus 10 using appropriate software and/or appropriate computer programs for this purpose. In this embodiment, the computing unit 26 is comprised by the system control unit 22 and/or incorporated within the system control unit 22. In an alternative embodiment of the disclosure, the computing unit 26 can also be implemented separately from the system control unit 22.

Control of the method for providing a process plan of a magnetic resonance examination is implemented when the corresponding software and/or computer programs are executed by means of a processor of the computing unit 26. Said software and/or computer programs can be stored in a memory unit of the computing unit 26 (not shown in more detail) or can be stored in a memory unit external to the computing unit 26, in which case the computing unit 26 can access the external memory unit by means of a data link.

In a first method step 100, an examination strategy is selected. The examination strategy may comprise a number n of metaprotocols MP which are required for clarifying the clinical and/or medical issue for the upcoming magnetic resonance examination. In addition to the number n of metaprotocols MP, the examination strategy also comprises a chronological order of the n metaprotocols MP with respect to one other. The examination strategy may be selected by a user, e.g. by a medical operator. The examination strategy may be selected by the user on the input unit 25 of the user interface 23. For this purpose, the user interface 23, e.g. the input unit 25, is controlled by the computing unit 26. By selecting and/or specifying the examination strategy, the computing unit 26 defines the number n of metaprotocols MP and also the order of the n metaprotocols MP relative to one another. For instance, the number n of metaprotocols MP and also the order of the n metaprotocols MP relative to one another is specified automatically and/or autonomously by the computing unit 26 of the magnetic resonance apparatus.

Each metaprotocol MP of the n metaprotocols MP comprises a protocol category having a plurality of different variants of a protocol P of the one protocol category. For example, a protocol category may comprise a transverse T1 measurement for a knee or other protocol categories, see FIG. 3. Each of the n metaprotocols MP may comprise a single protocol category. The different variants of the protocol P of the single protocol category of a metaprotocol MP may differ, for example, with respect to hardware attributes of hardware available for the magnetic resonance examination. The different variants of the protocol P of the single protocol category of a metaprotocol MP may also differ in respect of license-related attributes, e.g. as to whether a step covered by a license may or may not be performed. In addition, the different variants of the protocol P of the single protocol category of a metaprotocol MP may differ with respect to a sequence parameter and/or a sequence attribute. For example, the sequence parameter and/or sequence attribute may include whether the variant of the protocol P comprises a 2D sequence or a 3D sequence.

At least one ith metaprotocol MPi, where 1≤i≤n, comprises two or more different variants of a protocol P of the respective protocol category. Each metaprotocol MP of the n metaprotocols MP may comprise two or more different variants of a protocol P of the respective protocol category. The individual variants of a protocol P of the one protocol category for each metaprotocol MP of the n metaprotocols MP may be stored and/or deposited in a memory unit and/or a database. The memory unit and/or the database can be comprised by the magnetic resonance imaging device 10 performing the magnetic resonance examination. In addition, it is also conceivable for the database and/or the memory unit to be implemented externally to the magnetic resonance apparatus 10. In this case, it is also possible for the database and/or the memory unit to be stored in a cloud. Here the magnetic resonance apparatus 10, e.g. a computing unit 26 of the magnetic resonance apparatus 10, may access the database and/or the memory unit via a data link.

At least one metaprotocol MP of the n metaprotocols MP comprises a minimum variant of a protocol P(min) of the one protocol category. The minimum variant of protocol P(min) of the one protocol category is available for selecting a variant of protocol P(min) of the one protocol category. Each metaprotocol MP of the n metaprotocols MP may comprise a minimum variant of a protocol P(min) of the one protocol category. The minimum variant of a protocol P(min) of the one protocol category may comprise a variant of a protocol P(min) that comprises minimum requirements for existing and/or available hardware and/or minimum requirements for available licenses for executing the variant of the protocol P(min) of the one protocol category. For instance, the minimum variant of a protocol P(min) of the one protocol category comprises a variant of a protocol P(min) that is executable on each scanner unit of a magnetic resonance apparatus 10 independently of existing and/or available license attributes and/or hardware attributes.

At least one metaprotocol MP of the n metaprotocols MP comprises a maximum variant of a protocol P(max) of the one protocol category. The maximum variant of the protocol P(max) of the one protocol category is available for selection of a variant of the protocol P(max) of the one protocol category. Each metaprotocol MP of the n metaprotocols MP may comprise a maximum variant of a protocol P of the one protocol category. The maximum variant of a protocol P(max) of the one protocol category may comprise a "best variant" and/or an "ideal variant" of a protocol P(max). For example, the maximum variant of a protocol P(max) of the one protocol category comprises a variant of a protocol P(max) that assumes maximum available hardware components and/or maximum possible license attributes for executing the variant of the protocol P(max) of the one protocol category. The maximum variant of a protocol P(max) of the one protocol category thus comprises the variant of a protocol P(max) which provides the most ideal image data for clarifying the clinical and/or medical issue when performing the magnetic resonance examination.

In another second method step 101, a variant of a protocol P of the one protocol category of the ith metaprotocol MPi is selected. A variant of a protocol P of the one protocol category of the ith metaprotocol MPi is selected by means of a selection logic of the computing unit 26. The selection logic can comprise software and/or computer programs executed by the computing unit 26 for selecting a variant of a protocol P of the one protocol category of the ith metaprotocol MPi.

The selection logic can select a variant of the protocol P of the one protocol category of the ith metaprotocol MPi depending on a hardware attribute of available hardware, e.g. depending on a design of the magnetic resonance apparatus 10 locally available for performing the magnetic resonance examination. The hardware attribute is determined by the selection logic prior to selection of a variant of the protocol P of the one protocol category of an ith metaprotocol MPi. Information regarding the hardware attribute may be stored in the memory unit and/or database and is here retrieved by the selection logic. In addition, it can also be the case that the one item of information regarding the hardware attribute is acquired by means of a separate query. Such a query can, for example, be made at regular intervals, such as e.g. quarterly or bi-annually, etc., by means of the user interface 23, controlled by the computing unit 26.

Alternatively or in addition, the selection logic can here select a variant of the protocol P of the one protocol category of the ith metaprotocol MPi depending on license information. The license information may comprise information as to whether at least one defined step may be executed during execution of the variant of the protocol P of the one protocol category of the ith metaprotocol MPi. For instance, the license information comprises information concerning a right of use for execution of at least one defined step of the variants of the protocol P of the one protocol category of the ith metaprotocol MPi. Here, the license information is acquired by the selection logic prior to selection of a variant of the protocol P of the one protocol category of the ith metaprotocol MPi. The license information can be retrieved by the selection logic from a database and/or a memory unit in which the license information is stored and/or deposited. In addition, it can also be the case that the license information is acquired by means of a query. Such a query may, for example, be made at regular intervals, such as in particular monthly, etc., by means of the user interface 23, controlled by the computing unit 26.

In addition, the two or more different variants of the protocol P of the one protocol category of the ith metaprotocol MPi may differ with respect to a sequence parameter and/or a sequence attribute. In this second method step 101, the selection logic can select a variant of the protocol P of the one protocol category of the ith metaprotocol MPi depending on the sequence parameter and/or on the sequence attribute.

In this second method step 101 it can also be the case that at least an ith metaprotocol MPi comprises a first variant of a protocol P of the one protocol category, said first variant of the protocol P of the one protocol category being stored in the database and/or the memory unit. In this case, the selection logic can be designed to create and/or generate a second variant of the protocol P of the one protocol category from the first variant of the protocol P of the one protocol category by means of a defined rule.

For each metaprotocol MP of the n metaprotocols MP, the selection logic may comprise one or more defined rules that create and/or generate another variant of a protocol P of the one protocol category from already existing variants of protocols P of the one protocol category. For example, the first variant of protocol P of the one protocol category may have a licensed step Y and/or a licensed feature Y. The defined rule applies to generating a new variant of the protocol P of the one protocol category from the existing variant of the protocol P of the one protocol category by omitting the licensed step Y and/or the licensed feature Y. In addition, the defined rule can cover further changes to the existing variant of protocol P of the one protocol category, such as when licensed step Y and/or licensed feature Y is omitted and a parameter and/or value Z is changed. For example, the first variant of a protocol P of the one protocol category may comprise a TSE T1 protocol with an SMS (Simultaneous Multi Slice) license. In this case, the defined rule for generating and/or creating a second protocol P of the one protocol category can include omitting the SMS license and additionally reducing a number of layers by 30%. A second variant of a protocol P of the one protocol category of the ith metaprotocol MPi created and/or generated in the second method step 101 by means of the selection logic can then be stored in the memory unit and/or in a database.

In this second method step, the selection logic selects the maximum variant of a protocol P(max) of the one protocol category when selecting a variant of a protocol P for the ith metaprotocol MPi, provided that all the license requirements for the selected examination strategy are met and maximum available hardware components for the magnetic resonance examination are present. If not all the requirements are met, another variant of a protocol P of the one protocol category is selected by the selection logic when selecting a variant of a protocol P for the ith metaprotocol MPi. In this case, the selection logic selects a corresponding variant of a protocol P of the one protocol category for the ith metaprotocol MPi depending on available hardware components and/or depending on available licenses and/or as a function of set sequence attributes.

In FIG. 3, this is illustrated with reference to an examination strategy for a transverse T1 magnetic resonance examination for a knee, wherein a 3D measurement is desired. Here, the maximal variant of the protocol P(max) comprises a SPACE sequence with the licensed feature Compressed Sensing (CS) and high resolution. For execution of the maximum variant, a magnetic resonance apparatus 10 with a high and/or a maximum number of coil channels of an available local RF antenna unit is available.

If, on the other hand, no CS license is available, but a high and/or maximum number of coil channels of a local RF antenna unit is still available, further options can be selected. If a 3D measurement is still desired, a variant of the protocol P(SPACE_A) can be selected by the selection logic which selects a SPACE sequence, but without CS, but with high resolution. If, on the other hand, a 2D measurement is desired and determination of the license information shows that an SMS license (Simultaneous Multi Slice license) is available, a variant of the protocol P(TSE_SMS_A) can be selected by the selection logic which selects a TSE sequence with SMS and high resolution. If, on the other hand, a 2D measurement is desired and determination of the license information shows that no SMS license (Simultaneous Multi Slice license) is available, a variant of the protocol P(TSE_A), a TSE sequence and high resolution can be selected by the selection logic.

The variants of the protocols P(max), P(TSE_A), P(SPACE_A), P(TSE_SMS_A) are deposited and/or stored in the database and/or the memory unit and can be directly retrieved by the selection logic in the second method step 101 for performing a magnetic resonance examination. In addition, further variants of protocols P can be derived and generated from the stored variants of the protocol P(TSE_A), P(SPACE_A), P(TSE_SMS_A) by means of defined rules. Using the example of the metaprotocol MP shown in FIG. 3, a new variant of the protocol P(SPACE) can be generated by the selection logic from the protocol P(SPACE_A) in the case where a system or more specifically a magnetic resonance apparatus 10 having a small number of acquisition channels is present and thus only a low resolution can be achieved. The selection logic can generate a new variant of the protocol P(TSE_SMS) from the protocol P(TSE_SMS_A) in the case where a system or more specifically a magnetic resonance apparatus 10 having a small number of acquisition channels is present and thus only a low resolution can be achieved. A new variant of the protocol P(TSE) can be generated by the selection logic from the protocol P(TSE_A) in the case where a system or more specifically a magnetic resonance apparatus 10 having a small number of acquisition channels is present and thus only a low resolution can be achieved. The protocol variant P(TSE) comprises at the same time the minimum variant of the protocol P(min), which can be executed on any system and/or magnetic resonance apparatus 10 independently of hardware configurations and/or license attributes.

The second method step 101 is repeated by the selection logic until a selection of a variant of a protocol P of the one protocol category has been made for all n metaprotocols MP. For example, the selection of a variant of a protocol P of the one protocol category of the ith metaprotocol MPi is independent of a selection of a variant of a protocol P of the one protocol category of an (i+1)th metaprotocol MP(i+1).

In a further, third method step 102, the process plan of the magnetic resonance examination comprising the n protocols P1 . . . Pn is provided. FIG. 4 shows a provided process plan of the magnetic resonance examination. In this embodiment, the process plan comprises the metaprotocols MP1, MP2, . . . MPn each with a selected variant of a protocol P1, P2, . . . Pn. The individual metaprotocols MP1, MP2, . . .

MPn or rather the individual protocols P1, P2, . . . Pn are shown in sequence with respect to a time axis t, whereby the time axis t determines the order of the individual metaprotocols MP1, MP2, . . . MPn or rather of the individual protocols P1, P2, . . . Pn.

The plan is initially provided by means of the computing unit 26. In addition, the provided process plan of the magnetic resonance examination can also be presented to the user by means of the display unit 24 of the user interface 23. Such a presentation on the display unit 24 is controlled by the computing unit 26.

In a further fourth but optional method step 103, the provided magnetic resonance examination is performed. Here, the individual protocols P1 . . . Pn selected are successively executed and image data is acquired by means of the scanner unit.

Although the disclosure has been illustrated and described in detail by the exemplary embodiments, the disclosure is not limited by the disclosed examples and other variations will be apparent to persons skilled in the art without departing from the scope of protection sought for the disclosure.

What is claimed is:

1. A method for providing a magnetic resonance examination process plan incorporating one or more protocols, comprising:
   selecting, via one or more processors, an examination strategy comprising one or more metaprotocols equal to the number of the one or more protocols, and a chronological order of the one or more metaprotocols,
   storing each one of the one or more metaprotocols in a memory, each one of the one or more metaprotocols being identified with a protocol category including a plurality of different protocol variants of a protocol that is associated with the protocol category,
   wherein each one of the one or more metaprotocols is stored in the memory occupying an amount of storage space that is less than an amount of storage space required to store each combination of protocol variants used for a magnetic resonance examination in a preconfigured form;
   iteratively selecting, via one or more processors, for each one of the one or more metaprotocols, one of the plurality of different protocol variants of a respective protocol category;
   generating, via one or more processors, the magnetic resonance examination process plan comprising each one of the iteratively selected plurality of different protocol variants; and
   utilizing, via one or more processors, the generated magnetic resonance examination process plan to perform a magnetic resonance examination.

2. The method as claimed in claim 1, wherein the act of iteratively selecting one of the plurality of different protocol variants comprises iteratively selecting one of the plurality of different protocol variants for each one of the plurality of metaprotocols using a selection logic.

3. The method as claimed in claim 2, wherein the act of iteratively selecting one of the plurality of different protocol variants comprises using the selection logic to iteratively select one of the plurality of different protocol variants for each one of the plurality of metaprotocols depending on a hardware attribute of available hardware for performing the magnetic resonance examination.

4. The method as claimed in claim 3, further comprising:
   determining the hardware attribute using the selection logic prior to iteratively selecting one of the plurality of different protocol variants for each one of the plurality of metaprotocols.

5. The method as claimed claim 2, wherein the act of iteratively selecting one of the plurality of different protocol variants comprises iteratively selecting the plurality of different protocol variants for each one of the plurality of metaprotocols depending on license information.

6. The method as claimed in claim 5, further comprising:
   determining the license information using the selection logic prior to iteratively selecting one of the plurality of different protocol variants for each one of the plurality of metaprotocols.

7. The method as claimed in claim 1, wherein at least one of the one or more metaprotocols comprises two or more different protocol variants of a protocol that is associated with the protocol category; and
   storing the two or more different protocol variants in a database.

8. The method as claimed in claim 7, wherein the two or more different protocol variants differ with respect to a sequence parameter and/or a sequence attribute, and
   wherein one of the plurality of different protocol variants of a respective protocol category are selected depending on the sequence parameter and/or the sequence attribute.

9. The method as claimed in claim 1, wherein at least one of the one or more metaprotocols comprises a minimum protocol variant of a respective protocol category, and
   wherein the minimum protocol variant is executable on a scanner unit of a magnetic resonance apparatus independently of available license attributes and/or independently of hardware attributes.

10. The method as claimed in claim 1, wherein at least one of the one or more metaprotocols comprises a maximum protocol variant of a respective protocol category, and
    wherein the maximum protocol variant is associated with maximum available hardware components and/or maximum possible license attributes.

11. The method as claimed in claim 2, wherein at least one of the one or more metaprotocol comprises a first protocol variant of a respective protocol category, and the first protocol variant is stored in a database, and further comprising:
    generating, via the selection logic, a second protocol variant of the respective protocol category using the first protocol variant via a predetermined rule.

12. The method as claimed in claim 1, further comprising:
    generating, using the selection logic, at least one new protocol variant of a respective protocol category of one of the one or more metaprotocols; and
    storing the new protocol variant in a database.

13. The method as claimed in claim 2, wherein the act of iteratively selecting one of the plurality of different protocol variants for at least a subset of the plurality of metaprotocols occurs independently of one another.

14. The method as claimed in claim 1, further comprising:
    periodically querying a hardware attribute of available hardware for performing the magnetic resonance examination such that the hardware attribute is determined prior to the act of iteratively selecting one of the plurality of different protocol variants for each one of the plurality of metaprotocols.

15. The method as claimed in claim 1, further comprising:
generating, for a metaprotocol from among the one or more metaprotocols, a further protocol variant using one of the plurality of different protocol variants of the protocol category identified with the metaprotocol.

16. A magnetic resonance apparatus, comprising:
a scanner; and
a computing system including selection logic, the computing system configured to provide a magnetic resonance examination process plan incorporating one or more protocols by:
    selecting an examination strategy comprising one or more metaprotocols equal to the number of the one or more protocols and a chronological order of the one or more metaprotocols,
    storing each one of the one or more metaprotocols in a memory, each one of the one or more metaprotocols being identified with a protocol category including a plurality of different protocol variants of a protocol that is associated with the protocol category;
    iteratively selecting for each one of the one or more metaprotocols, one of the plurality of different protocol variants of a respective protocol category,
wherein each one of the one or more metaprotocols is stored in the memory occupying an amount of storage space that is less than an amount of storage space required to store each combination of protocol variants used for a magnetic resonance examination in a pre-configured form;
    generating the magnetic resonance examination process plan comprising each one of the iteratively selected plurality of different protocol variants; and
    utilizing the generated magnetic resonance examination process plan to perform a magnetic resonance examination.

17. A non-transitory computer-readable medium having instructions started thereon that, when executed by a control system associated with a magnetic resonance apparatus, cause the magnetic resonance apparatus to provide a magnetic resonance examination process plan incorporating one or more protocols by:
    selecting an examination strategy comprising one or more metaprotocols equal to the number of the one or more protocols and a chronological order of the one or more metaprotocols,
    storing each one of the one or more metaprotocols in a memory, each one of the one or more metaprotocols being identified with a protocol category including a plurality of different protocol variants of a protocol that is associated with the protocol category;
    wherein each one of the one or more metaprotocols is stored in the memory occupying an amount of storage space that is less than an amount of storage space required to store each combination of protocol variants used for a magnetic resonance examination in a pre-configured form;
    iteratively selecting for each one of the one or more metaprotocols, one of the plurality of different protocol variants of a respective protocol category;
    generating the magnetic resonance examination process plan comprising each one of the iteratively selected plurality of different protocol variants; and
    utilizing the generated magnetic resonance examination process plan to perform a magnetic resonance examination.

* * * * *